(12) United States Patent
Umemura et al.

(10) Patent No.: US 10,295,335 B2
(45) Date of Patent: May 21, 2019

(54) SHAPE MEASUREMENT APPARATUS AND SHAPE MEASUREMENT METHOD

(71) Applicant: NIPPON STEEL & SUMITOMO METAL CORPORATION, Tokyo (JP)

(72) Inventors: Jun Umemura, Tokyo (JP); Hironao Yamaji, Tokyo (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 0 days.

(21) Appl. No.: 15/567,664

(22) PCT Filed: Apr. 22, 2016

(86) PCT No.: PCT/JP2016/062806
§ 371 (c)(1),
(2) Date: Oct. 19, 2017

(87) PCT Pub. No.: WO2016/171265
PCT Pub. Date: Oct. 27, 2016

(65) Prior Publication Data
US 2018/0106607 A1  Apr. 19, 2018

(30) Foreign Application Priority Data
Apr. 22, 2015 (JP) .................. 2015-087518

(51) Int. Cl.
G01B 11/25 (2006.01)
G01B 11/255 (2006.01)
(Continued)

(52) U.S. Cl.
CPC .......... G01B 11/255 (2013.01); G01B 11/026 (2013.01); G01B 11/24 (2013.01);
(Continued)

(58) Field of Classification Search
CPC ... G01B 11/25; G01B 11/026; G01B 11/2518; G01M 11/0257; G01N 15/1463; G03F 7/70666; G01C 3/20
See application file for complete search history.

(56) References Cited

U.S. PATENT DOCUMENTS 5,691,815 A     11/1997  Huber et al.
7,436,525 B2 *  10/2008  Mukai ................ G01B 11/2518
                                                       356/601
(Continued)

FOREIGN PATENT DOCUMENTS

JP    2003-075137 A    3/2003
JP    2004-003930 A    1/2004
(Continued)

OTHER PUBLICATIONS

Office Action dated Jul. 25, 2018, in Korean Patent Application No. 10-2017-7032770, with partial English translation.
(Continued)

Primary Examiner — Tri T Ton
Assistant Examiner — Rebecca C Bryant
(74) Attorney, Agent, or Firm — Birch, Stewart, Kolasch & Birch, LLP

(57) ABSTRACT

[Object] To provide a shape measurement apparatus that, in measuring the unevenness shape of a measurement object by a light-section method, enables the shape of the measurement object to be measured precisely even when the distance between the measurement object and an image capturing apparatus fluctuates.
[Solution] Provided is a shape measurement apparatus including: a linear light position detection unit that detects, from a captured image of linear light applied to a measurement object by a linear light irradiation apparatus that is captured by an image capturing apparatus, a linear light position of the linear light; a distance computation unit that
(Continued)

computes a distance from the image capturing apparatus to the measurement object, on the basis of a distance difference between a reference linear light position detected by the linear light position detection unit when the measurement object is positioned at a position of a predetermined reference distance from the image capturing apparatus and the linear light position detected by the linear light position detection unit, the reference distance, and an angle formed by an optical axis of the image capturing apparatus and an emission direction of the linear light; a focus adjustment unit that adjusts focus of the image capturing apparatus on the basis of the distance from the image capturing apparatus to the measurement object; and a shape computation unit that computes a shape of the measurement object on the basis of the captured image.

8 Claims, 8 Drawing Sheets

(51) Int. Cl.
    *G01B 11/24* (2006.01)
    *G01B 11/02* (2006.01)
    *G06F 17/11* (2006.01)
    *G01B 11/30* (2006.01)
    G01N 15/14 (2006.01)
    G01M 11/02 (2006.01)
    G03F 7/20 (2006.01)
    G01C 3/20 (2006.01)
    G06T 7/521 (2017.01)

(52) U.S. Cl.
    CPC ........ *G01B 11/2522* (2013.01); *G01B 11/303* (2013.01); *G06F 17/11* (2013.01); *G01C 3/20* (2013.01); *G01M 11/0257* (2013.01); *G01N 15/1463* (2013.01); *G03F 7/70666* (2013.01); *G06T 7/521* (2017.01)

(56) References Cited

U.S. PATENT DOCUMENTS

| | | | |
|---|---|---|---|
| 2003/0043277 | A1 | 3/2003 | Kamon |
| 2007/0285672 | A1 | 12/2007 | Mukai et al. |

FOREIGN PATENT DOCUMENTS

| | | | |
|---|---|---|---|
| JP | 2008-070374 A | 3/2008 | |
| JP | 2009-145072 A | 7/2009 | |
| JP | 2010-071722 A | 4/2010 | |
| JP | 2012-112779 A | 6/2012 | |

OTHER PUBLICATIONS

Extended European Search Report dated Jul. 26, 2018, in European Patent Application No. 16783286.4.
Office Action dated Nov. 28, 2017, in Japanese Patent Application No. 2017-514219, with English translation.
International Search Report (PCT/ISA/210) issued in PCT/JP2016/062806, dated Jul. 19, 2016.
Written Opinion (PCT/ISA/237) issued in PCT/JP2016/062806, dated Jul. 19, 2016.

* cited by examiner

SHAPE MEASUREMENT APPARATUS AND SHAPE MEASUREMENT METHOD

TECHNICAL FIELD

The present invention relates to a shape measurement apparatus and a shape measurement method that measure the shape of a measurement object by a light-section method.

BACKGROUND ART

A light-section method is a technique of capturing, by an image capturing apparatus, an image of a line of light applied to a measurement object using a laser or the like, and measuring the unevenness shape of the measurement object from the degree of bend of the line of light detected from the captured image. For example, Patent Literature 1 discloses a technique of capturing an image of laser light applied to a measurement object using a time delay integration (TDI) camera, and measuring the shape of the measurement object on the basis of the obtained striped image.

The light-section method will be described in detail. As illustrated in FIG. 7, first, a linear light irradiation apparatus 10 that applies linear light, such as line laser or slit light, irradiates a measurement object 5 with linear light. Then, an image capturing apparatus 20 captures an image of linear light applied to the measurement object 5, and outputs a captured image A to an image processing apparatus 50. For example, when a measurement surface 5a of the measurement object 5, which is an irradiation surface irradiated with linear light, is flat, straight linear light appears in the captured image A. However, when the measurement surface 5a has a depression, linear light 12 that includes a bent part 12b due to the depression in a straight part 12a appears in the captured image A, as illustrated in FIG. 7. Thus, the shape of the measurement surface 5a can be measured on the basis of the degree of bend of the linear light 12 included in the captured image A, which is acquired by capturing an image of the measurement surface 5a of the measurement object 5 irradiated with the linear light 12.

In measuring the shape of the measurement object 5 from the captured image A by such a technique, in order to accurately find the degree of bend of the linear light 12 in the shot image and maintain the precision of shape measurement, it is necessary to achieve focus so that the linear light 12 is shown thin and clear in the shot image A. This requires the focus of the image capturing apparatus 20 to be accurately adjusted to be set on the measurement surface 5a of the measurement object 5. For example, in the case of measuring the shape of a side surface or a top surface of the measurement object 5 moving on a conveyance line, the image capturing apparatus 20 needs to be accurately focused on the side surface or the top surface of the measurement object 5. However, the shape of the measurement object 5 is not constant because, for example, specifications of products differ in a production line; for example, in the case where the measurement object 5 is a rectangular parallelepiped, size, such as width and height, differs.

If the width and height of the measurement object 5 is found before shape measurement, the distance from the installation position of the image capturing apparatus 20 to the measurement surface 5a of the measurement object 5 is calculated, and focus of the image capturing apparatus 20 is adjusted in accordance with the distance; thus, a clear image can be acquired. For example, in the case of measuring the shape of a side surface of the measurement object 5, as illustrated in FIG. 8, assume that a control apparatus 60 is notified of the width of the measurement object 5 before the start of measurement, and a distance D from the image capturing apparatus 20 to the measurement surface 5a is known. In addition, a focus ring 24 of the image capturing apparatus 20 that adjusts the position of a focus lens 22 is configured to be rotatable by a drive device, such as a motor. Thus, the control apparatus 60 drives the motor in accordance with the distance D from the installation position of the image capturing apparatus 20 to the measurement surface 5a of the measurement object 5 to rotate the focus ring 24 of the focus lens 22, thereby focusing the image capturing apparatus 20 on the measurement surface 5a. Alternatively, if the depth of field of the image capturing apparatus 20 is sufficiently deep, a clear image can be obtained without adjustment of focus in some cases.

CITATION LIST

Patent Literature

Patent Literature 1: JP 2004-3930A

SUMMARY OF INVENTION

Technical Problem

However, the size (e.g., width) of a measurement object is not found beforehand in some cases. Alternatively, even if the size of a measurement object is found beforehand, in the event of slanted movement in which the measurement object 5 moves in a state of being inclined with respect to a conveyance direction as illustrated in FIG. 9, or position deviation in which the width center of the measurement object 5 is deviated from the center C in the width direction of the conveyance line as illustrated in FIG. 10, the focus of the image capturing apparatus 20 is off the measurement surface 5a of the measurement object 5, resulting in a blurred, unclear image.

As a coping method for the focus of the image capturing apparatus 20 being off the measurement surface 5a of the measurement object 5, for example, it is possible to install a distance sensor, and adjust focus on the basis of a measured distance between the image capturing apparatus 20 and the measurement surface 5a measured by the distance sensor. However, it is necessary to additionally install a distance sensor, which complicates device configuration. In addition, as a method not using a distance sensor, it is possible to calculate contrast of luminance from images continuously captured while moving a focus lens to and fro in the optical axis direction of the image capturing apparatus, and adjust focus by searching for a position with high contrast. However, this method takes time until focus is achieved and leads to poor responsivity, and thus is difficult to apply to a measurement object that is being conveyed.

Hence, the present invention is made in view of the above problems, and an object of the present invention is to provide a novel and improved shape measurement apparatus and shape measurement method that, in measuring the unevenness shape of a measurement object by a light-section method, enable the shape of the measurement object to be measured precisely even when the distance between the measurement object and an image capturing apparatus fluctuates.

Solution to Problem

According to an aspect of the present invention in order to achieve the above-mentioned object, there is provided a shape measurement apparatus including: a linear light position detection unit that detects, from a captured image of linear light applied to a measurement object by a linear light irradiation apparatus that is captured by an image capturing apparatus, a linear light position of the linear light; a distance computation unit that computes a distance from the image capturing apparatus to the measurement object, on the basis of a distance difference between a reference linear light position detected by the linear light position detection unit when the measurement object is positioned at a position of a predetermined reference distance from the image capturing apparatus and the linear light position detected by the linear light position detection unit, the reference distance, and an angle formed by an optical axis of the image capturing apparatus and an emission direction of the linear light; a focus adjustment unit that adjusts focus of the image capturing apparatus on the basis of the distance from the image capturing apparatus to the measurement object; and a shape computation unit that computes a shape of the measurement object on the basis of the captured image.

The distance computation unit may compute the distance from the image capturing apparatus to the measurement object on the basis of a distance function expressed using an image capturing resolution of the image capturing apparatus.

For example, the distance computation unit may compute a distance D from the image capturing apparatus to the measurement object on the basis of Formula (A) below. Alternatively, the distance computation unit may compute a distance D from the image capturing apparatus to the measurement object on the basis of Formula (B) below.

[Math. 1]

$$D = D_0 + \frac{X_e r_0 / \tan\theta}{1 - X_e r_0 / \tan\theta / D_0} \quad (A)$$

$$D = D_0 + X_e r_0 \tan\theta \quad (B)$$

Here, $D_0$ is the reference distance, $r_0$ is an image capturing resolution at the reference distance, Xe is a distance difference between the linear light position and the reference linear light position in units of pixels of the captured image, and θ is an angle formed by the optical axis of the image capturing apparatus and the emission direction of the linear light.

The linear light position detection unit may calculate a projection waveform expressing a sum of luminance values of pixels aligned in a straight-line direction of linear light at each position in a direction orthogonal to the straight-line direction of the linear light in the captured image, and set a peak position of the projection waveform as the linear light position.

Alternatively, the linear light position detection unit may calculate a projection waveform expressing a sum of luminance values of pixels aligned in a straight-line direction of linear light at each position in a direction orthogonal to the straight-line direction of the linear light in the captured image, and set a center-of-gravity position of the projection waveform as the linear light position.

The shape computation unit may compute the shape of the measurement object on the basis of a maximum luminance position in a direction orthogonal to a straight-line direction of the linear light that is calculated for each position in the straight-line direction in the captured image.

Alternatively, the shape computation unit may compute the shape of the measurement object on the basis of a center-of-gravity position of luminance in a direction orthogonal to a straight-line direction of the linear light that is calculated for each position in the straight-line direction in the captured image.

According to another aspect of the present invention in order to achieve the above-mentioned object, there is provided a shape measurement method including: a linear light position detection step of detecting, from a captured image of linear light applied to a measurement object by a linear light irradiation apparatus that is captured by an image capturing apparatus, a linear light position of the linear light; a distance computation step of computing a distance from the image capturing apparatus to the measurement object, on the basis of a distance difference between a reference linear light position detected when the measurement object is positioned at a position of a predetermined reference distance from the image capturing apparatus and the linear light position, the reference distance, and an angle formed by an optical axis of the image capturing apparatus and an emission direction of the linear light; a focus adjustment step of adjusting focus of the image capturing apparatus on the basis of the distance from the image capturing apparatus to the measurement object; and a shape computation step of computing a shape of the measurement object on the basis of the captured image.

Advantageous Effects of Invention

As described above, according to the present invention, in measuring the unevenness shape of a measurement object by a light-section method, the shape of the measurement object can be measured precisely even when the distance between the measurement object and an image capturing apparatus fluctuates.

DESCRIPTION OF EMBODIMENTS

Figure 1:
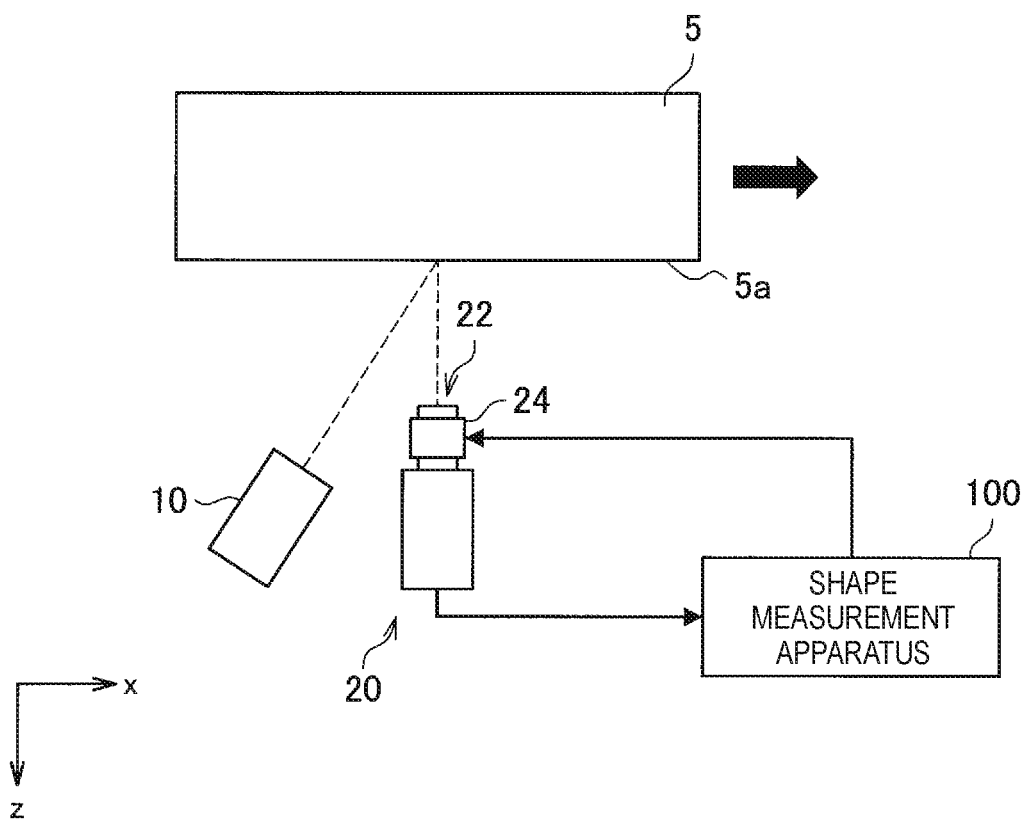
FIG. 1 is an explanatory diagram illustrating a schematic configuration of a shape measurement system that measures the shape of a measurement object by a light-section method.

Hereinafter, (a) preferred embodiment(s) of the present invention will be described in detail with reference to the appended drawings. In this specification and the appended drawings, structural elements that have substantially the same function and structure are denoted with the same reference numerals, and repeated explanation of these structural elements is omitted.

<1. Configuration>

Figure 2:
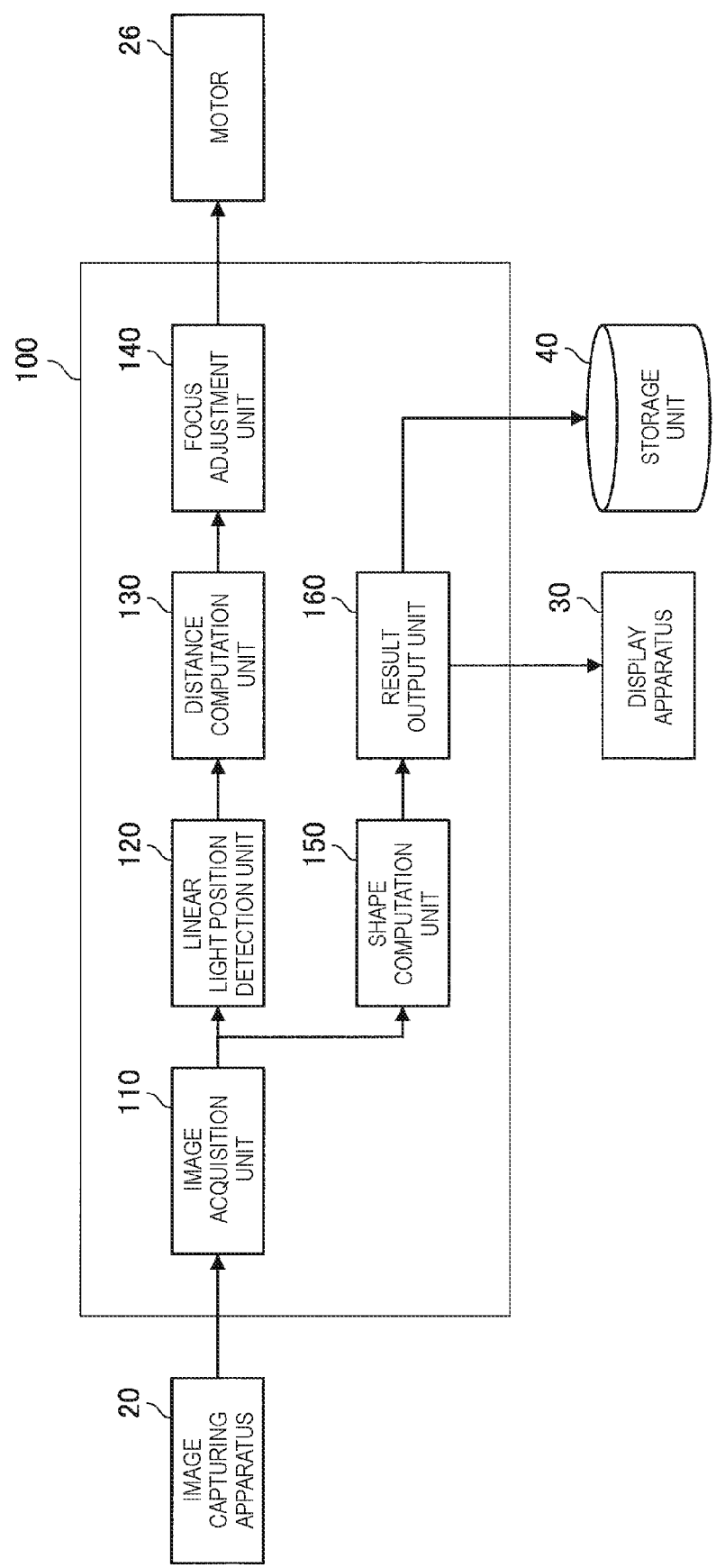
FIG. 2 is a functional block diagram illustrating a functional configuration of a shape measurement apparatus according to an embodiment of the present invention.
Figure 7:
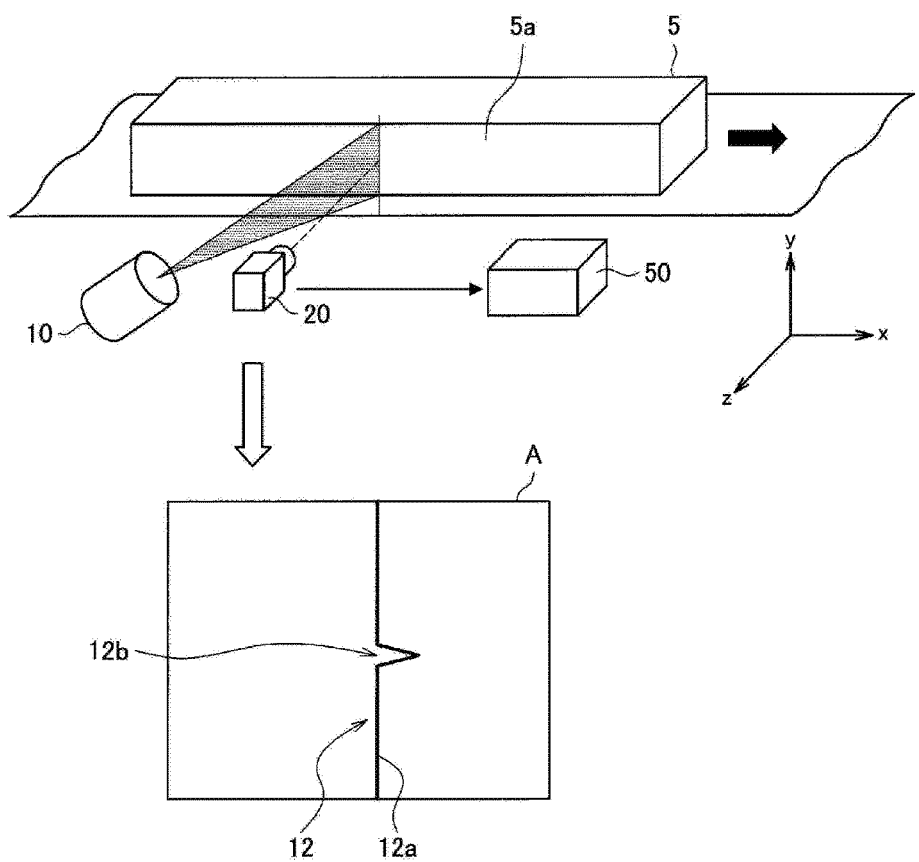
FIG. 7 is an explanatory diagram for explaining the principle of a light-section method.
Figure 8:
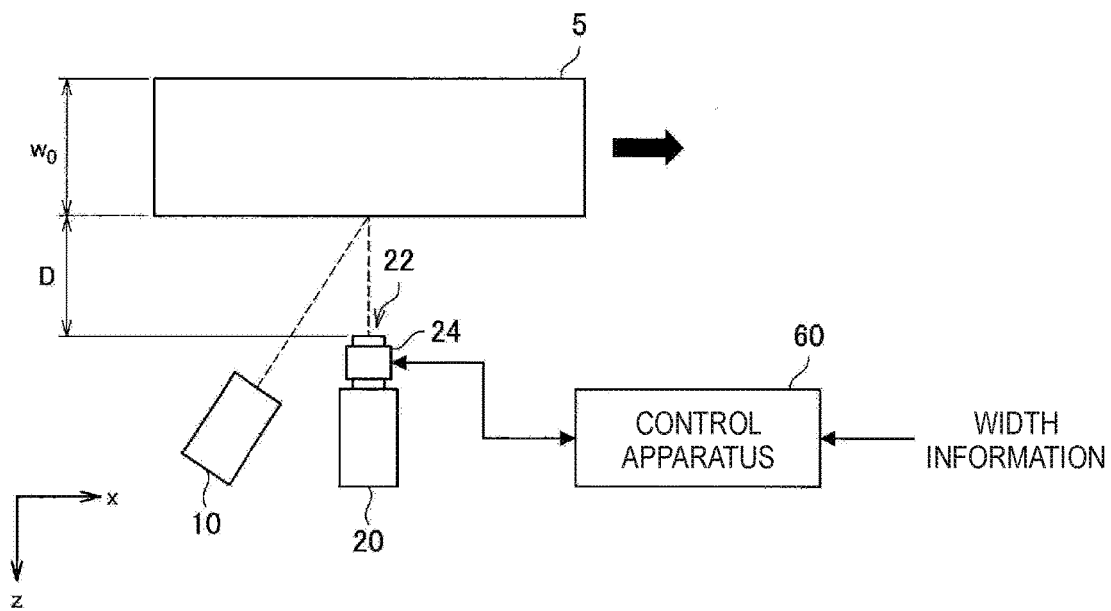
FIG. 8 is an explanatory diagram illustrating an example of a coping method for a change in width of a measurement object.
Figure 9:
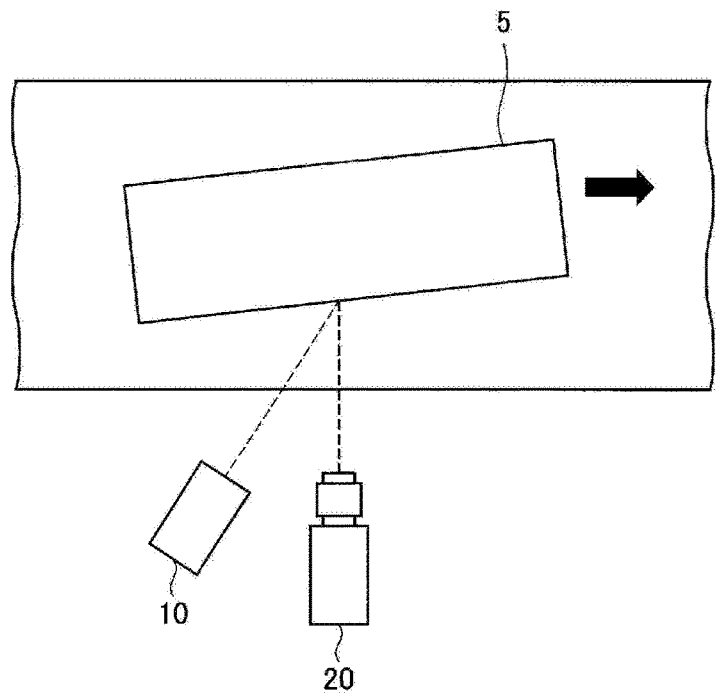
FIG. 9 is an explanatory diagram for explaining slanted movement of a measurement object that serves as a cause of defocus.
Figure 10:
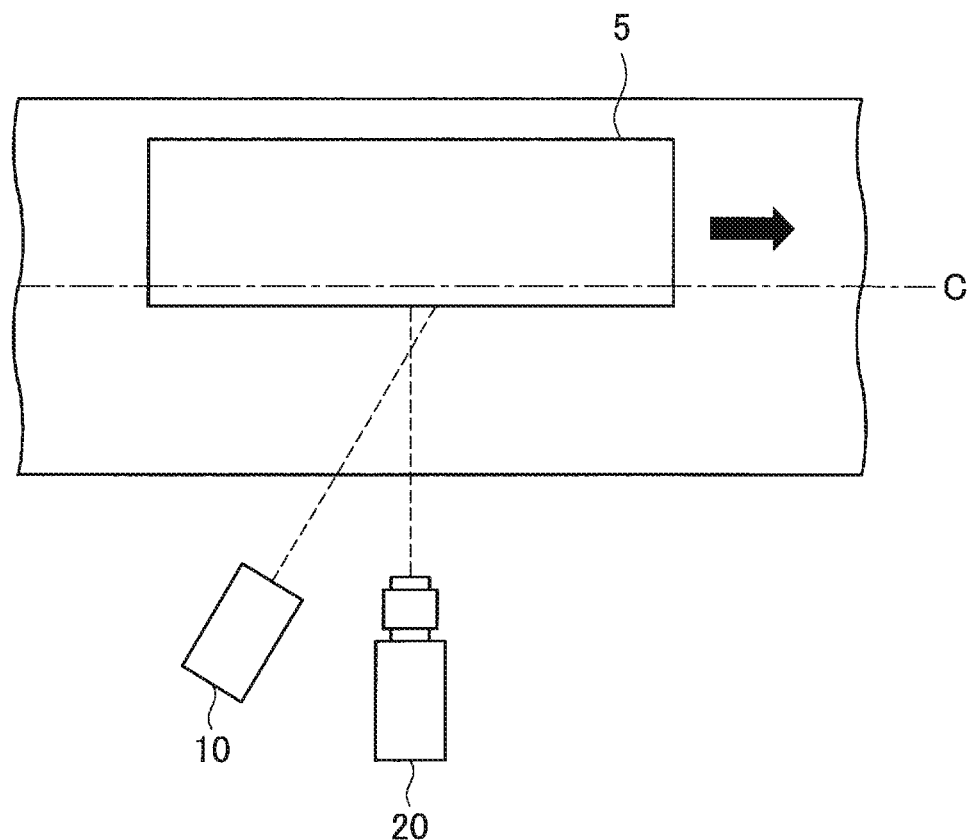
FIG. 10 is an explanatory diagram for explaining position deviation of a measurement object that serves as a cause of defocus.

First, a configuration of a shape measurement apparatus according to an embodiment of the present invention is described with reference to FIGS. 1 and 2. FIG. 1 is an explanatory diagram illustrating a schematic configuration of a shape measurement system that measures the shape of a measurement object 5 by a light-section method. FIG. 2 is a functional block diagram illustrating a functional configuration of a shape measurement apparatus according to the present embodiment. Note that FIG. 1 illustrates a state of viewing the measurement object 5 in a plan view, and one side surface of the measurement object 5 that is a rectangular parallelepiped as illustrated in FIG. 7 serves as a measurement surface 5a.

[1-1. Schematic Configuration of Shape Measurement System]

A shape measurement system is a system that measures the shape of the measurement object 5 by a light-section method. As illustrated in FIG. 1, the shape measurement system includes a linear light irradiation apparatus 10 that irradiates the measurement object 5 with linear light, an image capturing apparatus 20 that captures an image of linear light applied to the measurement object 5, and a shape measurement apparatus 100 that specifies the unevenness shape of the measurement surface 5a of the measurement object 5, on the basis of a captured image captured by the image capturing apparatus 20. The linear light irradiation apparatus 10 is an apparatus capable of outputting linear light, such as line laser or slit light. As the image capturing apparatus 20, an area camera can be used, for example.

The shape measurement apparatus 100 according to the present embodiment adjusts focus of the image capturing apparatus 20 in accordance with the distance between the measurement object 5 and the image capturing apparatus 20. Thus, even when the distance between the measurement object 5 and the image capturing apparatus 20 fluctuates, the position of a focus lens 22 of the image capturing apparatus 20 is controlled so that a clear image is acquired, which enables the shape of the measurement object 5 to be measured precisely. In the present embodiment, the image capturing apparatus 20 includes the focus lens 22 having a focus ring 24 that is rotated by a drive device such as a motor. That is, the shape measurement apparatus 100 drives the motor in accordance with the distance from the installation position of the image capturing apparatus 20 to the measurement surface 5a of the measurement object 5 to rotate the focus ring 24 of the focus lens 22, thereby achieving focus.

The shape measurement apparatus 100 according to such an embodiment performs shape measurement processing of specifying the shape of the measurement object 5 on the basis of a captured image, and focus adjustment processing of adjusting focus of the image capturing apparatus 20 on the basis of a captured image.

In shape measurement processing, by a light-section method, an image of a line of light applied to a measurement object is captured by an image capturing apparatus, and the unevenness shape of the measurement object is measured from the degree of bend of linear light detected from the captured image. As illustrated in FIG. 1, when the linear light irradiation apparatus 10 irradiates the measurement object 5 with linear light, an image of linear light applied to the measurement object 5 is captured by the image capturing apparatus 20, and a captured image is output to the shape measurement apparatus 100. The shape measurement apparatus 100 measures the shape of the measurement surface 5a on the basis of the degree of bend of the linear light included in the captured image, which is acquired by capturing an image of the measurement surface 5a of the measurement object 5 irradiated with the linear light 12

In focus adjustment processing, focus is set on the measurement surface 5a in accordance with fluctuation of the distance between the image capturing apparatus 20 and the measurement surface 5a of the measurement object 5. In the present embodiment, the distance between the image capturing apparatus 20 and the measurement surface 5a of the measurement object 5 is acquired on the basis of a captured image acquired by the image capturing apparatus 20, and focus of the image capturing apparatus 20 is adjusted by the shape measurement apparatus 100. Executing the focus adjustment processing in parallel with the shape measurement processing or executing them alternately enables the shape of the measurement object to be measured precisely even when the distance between the measurement object and the image capturing apparatus fluctuates.

[1-2. Configuration of Shape Measurement Apparatus]

The shape measurement apparatus 100 will be described in detail. As illustrated in FIG. 2, the shape measurement apparatus 100 includes an image acquisition unit 110, a linear light position detection unit 120, a distance computation unit 130, a focus adjustment unit 140, a shape computation unit 150, and a result output unit 160. Of these, the linear light position detection unit 120, the distance computation unit 130, and the focus adjustment unit 140 are functional units that execute focus adjustment processing of adjusting the focus of the image capturing apparatus 20. The shape computation unit 150 and the result output unit 160 are functional units that execute shape specifying processing of specifying the shape of the measurement object 5.

The image acquisition unit 110 is an interface unit that acquires a captured image captured by the image capturing apparatus 20. The image captured by the image capturing apparatus 20 is sequentially input to the image acquisition unit 110. The image acquisition unit 110 outputs the input captured image to the linear light position detection unit 120 and the shape computation unit 150.

The linear light position detection unit 120 detects a linear light position of linear light in the captured image by arithmetic processing. For example, in the captured image, the straight-line direction of linear light is set as a vertical direction, and a direction orthogonal to the straight-line direction of linear light is set as a horizontal direction, and the linear light position detection unit 120 first takes the sum of luminance values of pixels aligned in the vertical direction at each position in the horizontal direction of the captured image, and acquires a projection in the vertical direction (hereinafter also referred to as a "projection waveform"). Then, the linear light position detection unit 120 specifies the linear light position in the captured image on the basis of the projection waveform. The linear light position in the captured image may be a peak position or a center-of-gravity position of the projection waveform, for example. The linear light position detection unit 120 outputs the calculated linear light position in the captured image to the distance computation unit 130.

The distance computation unit 130 calculates the distance between the image capturing apparatus 20 and the measurement object 5, on the basis of the linear light position in the captured image calculated by the linear light position detection unit 120. The distance computation unit 130 geometrically calculates the distance between the image capturing apparatus 20 and the measurement object 5 on the basis of the linear light position in the captured image and installation positions of the linear light irradiation apparatus 10 and the image capturing apparatus 20 with respect to a reference plane that is away from the image capturing apparatus 20 by a reference distance decided in advance. Note that details of calculation processing of the distance between the image capturing apparatus 20 and the measurement object 5 by the distance computation unit 130 are described later. The distance computation unit 130 outputs the calculated distance between the image capturing apparatus 20 and the measurement object 5 to the focus adjustment unit 140.

The focus adjustment unit 140 adjusts the focus position of the focus lens 22 of the image capturing apparatus 20 on the basis of the distance between the image capturing apparatus 20 and the measurement object 5 calculated by the distance computation unit 130. As illustrated in FIG. 1, the focus lens 22 according to the present embodiment is a motor drive lens including a motor 26 that rotates the focus ring 24. The focus adjustment unit 140 outputs, to the motor 26, a command to move the focus lens 22 so that focus is set on the measurement surface 5a, on the basis of the distance between the image capturing apparatus 20 and the measurement object 5. The motor 26 is a stepping motor, for example. The focus adjustment unit 140 adjusts focus by, for example, causing the motor 26 to rotate the focus ring 24 so that the lens is positioned at a distance position where focus is achieved, which is away from the measurement surface 5a of the measurement object 5 by a predetermined distance. The focus adjustment unit 140 may keep, in advance, a correspondence relationship between the distance from the image capturing apparatus 20 to the measurement surface 5a and a rotation angle of the focus ring 24 at which focus is achieved. For example, this correspondence relationship may be obtained by a technique such as setting a plurality of distances from the image capturing apparatus 20, capturing an image of a sample at each distance, and acquiring, in advance, the rotation angle of the focus ring 24 at which focus is set on the sample at each distance.

The shape computation unit 150 calculates the unevenness shape of the measurement surface 5a of the measurement object 5 on the basis of the degree of bend of the linear light in the captured image. The shape computation unit 150 specifies a position in the horizontal direction that exhibits the maximum luminance at each position in the vertical direction of the captured image, and calculates the unevenness shape of the measurement surface 5a of the measurement object 5. Note that details of calculation processing of the shape of the measurement object 5 by the shape computation unit 150 are described later. The shape computation unit 150 outputs the calculated shape of the measurement object 5 to the result output unit 160.

The result output unit 160 outputs the shape of the measurement surface 5a of the measurement object 5 calculated by the shape computation unit 150 to a display apparatus 30 and a storage unit 40. The display apparatus 30 may be a display provided for the shape measurement apparatus 100, or may be a display capable of outputting also display information from a device other than the shape measurement apparatus 100. Displaying the calculated shape of the measurement surface 5a of the measurement object 5 on the display apparatus 30 enables an operator to be notified of the shape of the measurement surface 5a of the measurement object 5. In addition, storing the shape of the measurement surface 5a of the measurement object 5 in the storage unit 40 makes it possible to specify a position having an unevenness shape on the measurement surface 5a of the measurement object 5, for example.

The functional configuration of the shape measurement apparatus 100 according to the present embodiment has been described.

<2. Processing by Shape Measurement Apparatus>

Next, processing performed by the shape measurement apparatus 100 according to the present embodiment is described on the basis of FIGS. 3 to 6. The shape measurement apparatus 100 according to the present embodiment performs shape measurement processing of specifying the shape of the measurement surface 5a of the measurement object 5 on the basis of a captured image, and focus adjustment processing of adjusting focus of the image capturing apparatus 20 on the basis of a captured image; thus, the shape of the measurement surface 5a of the measurement object can be measured precisely even when the distance between the measurement object and the image capturing apparatus fluctuates.

Figure 3:
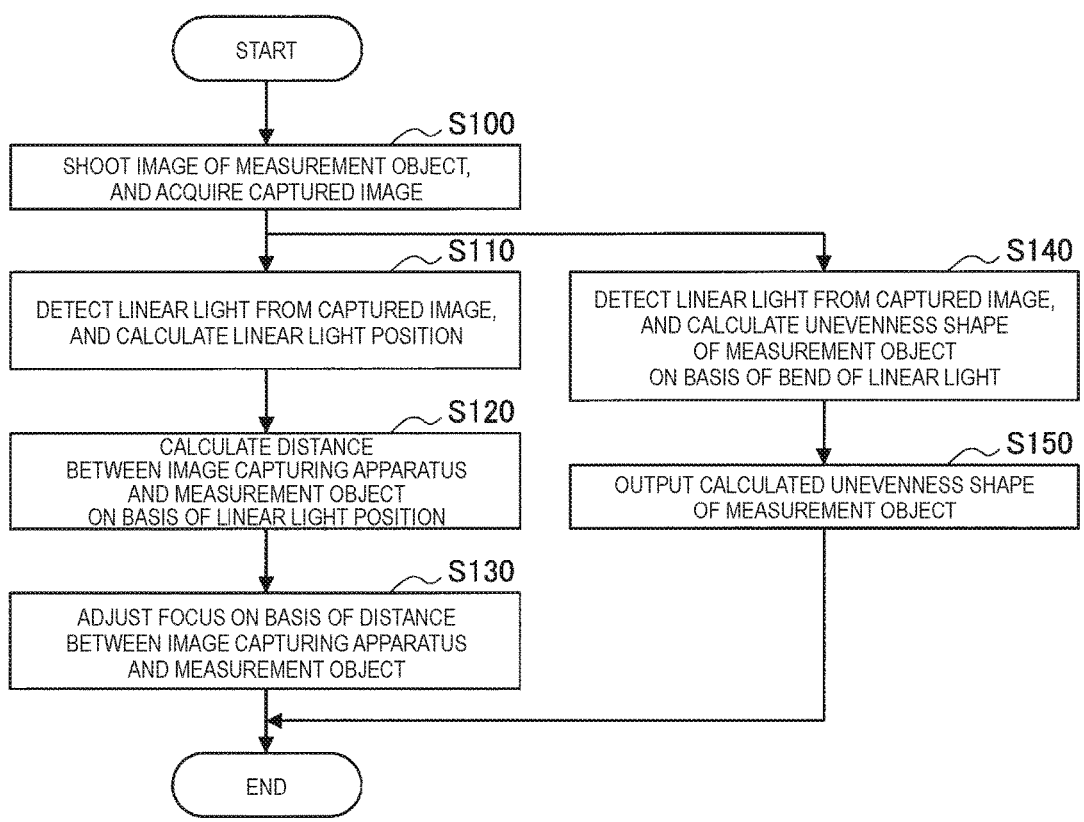
FIG. 3 is a flowchart illustrating processing performed by a shape measurement apparatus according to the embodiment.

First, an image of the measurement surface 5a of the measurement object 5 irradiated with linear light is captured by the image capturing apparatus 20, and the captured image captured by the image capturing apparatus 20 is output to the shape measurement apparatus 100 at a predetermined timing. As illustrated in FIG. 3, when the image acquisition unit 110 acquires the captured image captured by the image capturing apparatus 20 (S100), the shape measurement apparatus 100 starts focus adjustment processing (S110 to S130) and shape measurement processing (S140, S150). The focus adjustment processing and the shape measurement processing may be executed in parallel or may be executed alternately. The processing will be described in detail.

[2-1. Focus Adjustment Processing]

Figure 4:
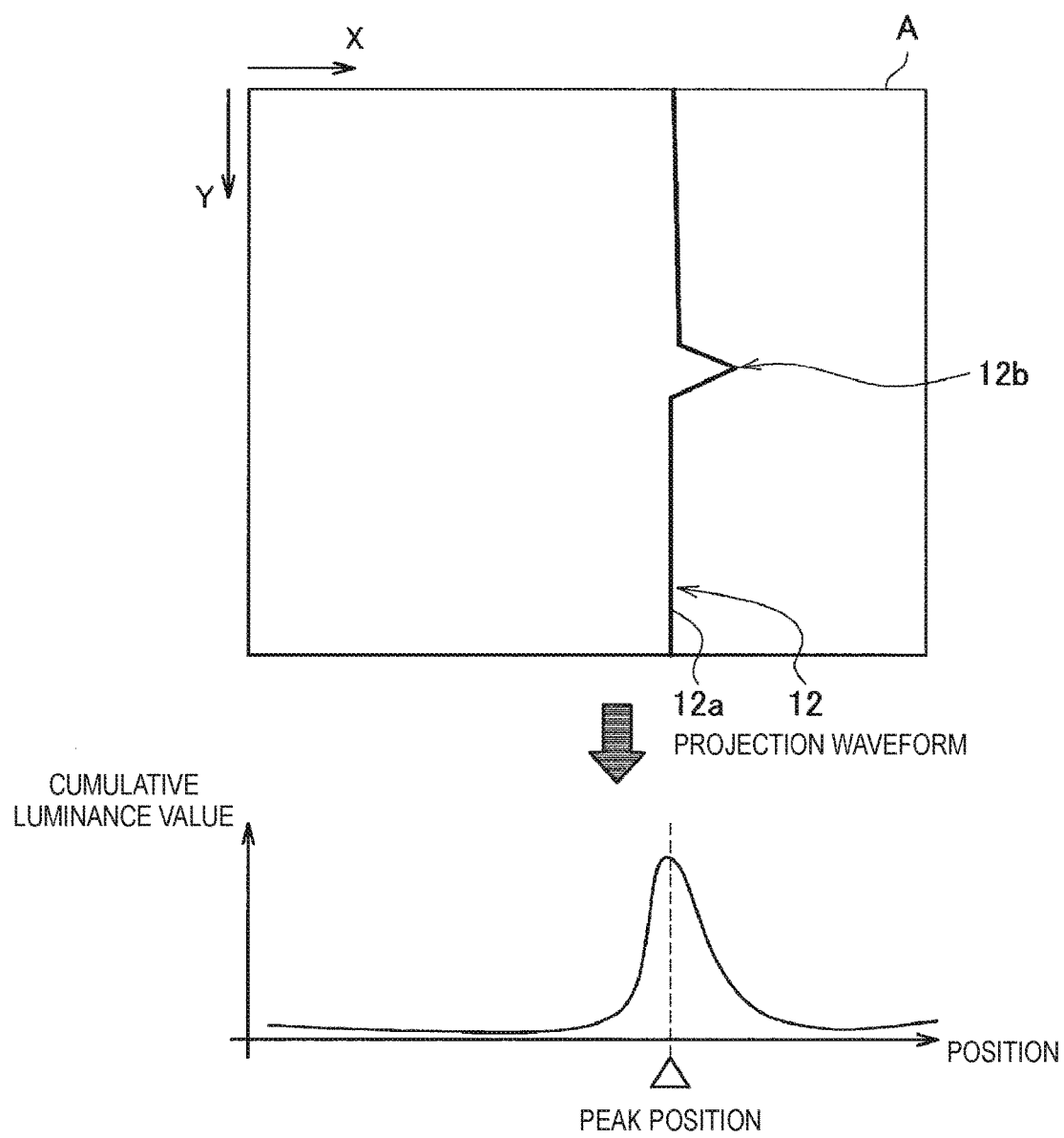
FIG. 4 is an explanatory diagram for explaining a method for calculating a linear light position in a captured image in step S110.

In the focus adjustment processing, first, the linear light position detection unit 120 calculates the linear light position of linear light in the captured image (S110). A method for calculating the linear light position in the captured image will be described on the basis of FIG. 4. The captured image A illustrated on the upper side of FIG. 4 is an example of an image of the measurement surface 5a of the measurement object 5 captured by the image capturing apparatus 20 in the shape measurement system with the configuration illustrated in FIG. 1. In the captured image A, the conveyance direction of the measurement object 5 is set as an X direction, and the straight-line direction of the linear light 12 orthogonal to the X direction is set as a Y direction. The captured image A is an image I(x, y) composed of N×M pixels ($0 \leq x \leq N-1$, $0 \leq y \leq M-1$). Here, x is the X-direction position of each pixel, and y is the Y-direction position of each pixel.

The linear light position detection unit 120 takes the sum (cumulative luminance value) of luminance values of pixels aligned in the straight-line direction of the linear light 12 (the vertical direction, the Y direction) at each position in the horizontal direction (the X direction) of the captured image A of FIG. 4, on the basis of Formula (1) below, to acquire a waveform expressing the cumulative luminance value at each position in the horizontal direction as illustrated on the lower side of FIG. 4. This waveform is referred to as a projection waveform. Since the linear light 12 extends in the vertical direction, the position of the linear light 12 appears as a peak in the projection waveform. The linear light position detection unit 120 specifies the linear light position in the captured image A on the basis of such a projection waveform.

More specifically, the linear light position appears in the captured image A with a luminance value different from that of a portion not irradiated with the linear light 12. Consequently, also in the projection waveform, the cumulative luminance value at a position irradiated with the linear light 12 is significantly higher than the cumulative luminance value at another position. Hence, the linear light position detection unit 120 detects a position with a significantly high cumulative luminance value in the projection waveform as a linear light position. The linear light position may be a peak position of the projection waveform as expressed by Formula (2) below, or may be a center-of-gravity position of the projection waveform as expressed by Formula (3) below, for example. Note that even if the captured image A from which the projection waveform is calculated is not focused on the measurement object 5, thus being unclear, the linear light position detection unit 120 can specify the linear light position as long as a peak appears in the projection waveform.

[Math. 2]

$$Proj(x) = \sum_{y=0}^{M-1} I(x, y) \quad (1)$$

$$\text{Peak position} = \operatorname{argmax}_x Proj(x) \quad (2)$$

$$\text{Center-of-gravity position} = \sum_{x=0}^{N-1} xProj(x) \Big/ \sum_{x=0}^{N-1} Proj(x) \quad (3)$$

When the linear light position is specified by the linear light position detection unit 120, next, the distance computation unit 130 calculates the distance between the image capturing apparatus 20 and the measurement object 5 at the time of acquiring the captured image, on the basis of the linear light position (S120). A method for calculating the distance between the image capturing apparatus 20 and the measurement object 5 will be described on the basis of FIG. 5.

Figure 5:
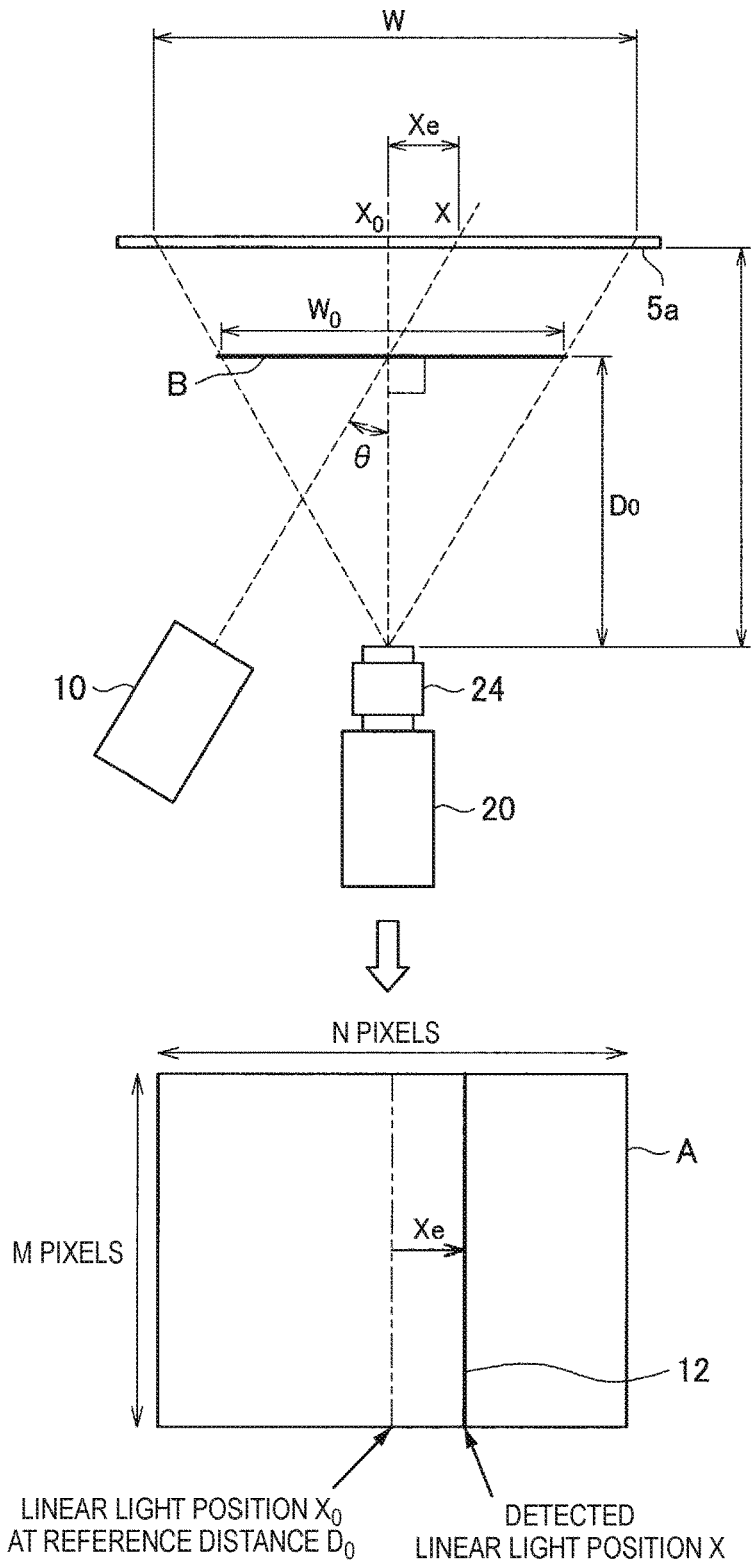
FIG. 5 is an explanatory diagram for explaining a method for calculating a distance between an image capturing apparatus and a measurement object in step S120.

FIG. 5 is a schematic diagram illustrating, in regard to the linear light irradiation apparatus 10 and the image capturing apparatus 20, a positional relationship between the measurement surface 5a of the measurement object 5 and a reference plane B that is away from the image capturing apparatus 20 by a reference distance $D_0$ in the optical axis direction of the image capturing apparatus 20. The reference distance $D_0$ is a fixed value set in advance for calculating a distance D from the image capturing apparatus 20 to the measurement surface 5a. For example, in the case where one side surface of the measurement object 5 serves as the measurement surface 5a as illustrated in FIG. 1, the distance between the image capturing apparatus 20 and a planned position where the measurement surface 5a originally is to be placed may be set as the reference distance $D_0$. Note that the planned position where the measurement surface 5a originally is to be placed is, for example, a position such that the width center of the measurement object 5 coincides with the center C in the width direction of the conveyance line. In addition, for example, in the case where the top surface of the measurement object 5 serves as the measurement surface 5a, the distance between the image capturing apparatus 20 and a planned position where the top surface originally is to be placed may be set as the reference distance $D_0$, as in the case where one side surface serves as the measurement surface 5a.

As illustrated in FIG. 5, the reference plane B positioned away from the image capturing apparatus 20 by the reference distance $D_0$ orthogonally intersects the optical axis of the image capturing apparatus 20 at its center. In the shape measurement system, the image capturing apparatus 20 is placed to be able to be focused on this reference plane B. In addition, the linear light irradiation apparatus 10 emits the linear light 12 from a direction inclined by an angle θ from the optical axis of the image capturing apparatus 20. On this occasion, the linear light irradiation apparatus 10 is placed in a manner that the linear light 12 intersects the optical axis of the image capturing apparatus 20 at the reference plane B. In this manner, the shape measurement system is configured in a manner that a clear image of the linear light 12 can be captured when the measurement surface 5a of the measurement object 5 is at the reference plane B.

Here, assume that the measurement surface 5a of the measurement object 5 is deviated from the position of the reference plane B in a direction going away from the image capturing apparatus 20. On this occasion, since focus is not set on the measurement surface 5a, the captured image A of the image capturing apparatus 20 is an unclear image. Hence, to move the focus lens 22 of the image capturing apparatus 20 to a position where focus is set on the measurement surface 5a, the distance computation unit 130 calculates the distance D from the image capturing apparatus 20 to the measurement surface 5a.

The distance D from the image capturing apparatus 20 to the measurement surface 5a is expressed by Formula (4) below. In Formula (4), d is the distance [mm] between the reference plane B and the measurement surface 5a, and is expressed by Formulas (5) and (6) below. In Formula (5), $X_0$ is a linear light position on the reference plane B (hereinafter also referred to as a "reference linear light position"), and X is an irradiation position of the linear light 12 that appears in the captured image A. For example, when the measurement object 5 is farther from the image capturing apparatus 20 than the reference plane B is as illustrated in FIG. 5, the distance D from the image capturing apparatus 20 to the measurement surface 5a is larger than the reference distance $D_0$. On this occasion, in the captured image A, a linear light position X appears on the right side of the drawing (the side opposite to the linear light irradiation apparatus 10) with respect to the linear light position $X_0$. When the measurement object 5 is closer to the image capturing apparatus 20 than the reference plane B is, the distance D from the image capturing apparatus 20 to the measurement surface 5a is smaller than the reference distance $D_0$. On this occasion, in the captured image A, a linear light position X appears on the left side of the drawing (the linear light irradiation apparatus 10 side) with respect to the linear light position $X_0$. Thus, in accordance with the distance D from the image capturing apparatus 20 to the measurement surface 5a, deviation (a distance difference Xe [pixel]) occurs between the linear light position $X_0$ and the linear light position X detected in step S110. A distance difference in real space corresponding to this Xe is Xe·r, where a shooting resolution at the distance D is r [mm/pixel], and d is expressed by Formula (5) on the basis of a geometric relationship. In addition, the shooting resolution r [mm/pixel] at the distance D is expressed by Formula (6), where the width of the field-of-view of the image capturing apparatus 20 at the distance D [mm] is W [mm].

[Math. 3]

$$D = D_0 + d \quad (4)$$

$$d = \frac{X - X_0}{\tan\theta} r = \frac{X_e}{\tan\theta} r \quad (5)$$

$$r = \frac{W}{N} \quad (6)$$

On the other hand, on the basis of a proportional relationship, the relation of Formula (7) below holds, where the width of the field-of-view of the image capturing apparatus 20 at the reference plane B (the reference distance $D_0$ [mm]) is $W_0$ [mm]. In addition, an image capturing resolution $r_0$ at the reference plane B is $W_0/N$; hence, $r_0$ and r satisfy the relation of Formula (8) below.

[Math. 4]

$$W = \frac{D}{D_0} W_0 \quad (7)$$

$$r = \frac{D}{D_0} r_0 \quad (8)$$

Hence, the distance D is expressed by Formula (9) below on the basis of Formulas (4), (5), and (7).

[Math. 5]

$$D = D_0 + \frac{X_e r_0 / \tan\theta}{1 - X_e r_0 / \tan\theta / D_0} \quad (9)$$

Here, the image capturing resolution $r_0$ at the reference distance $D_0$ is expressed by Formula (10) below on the basis of Formula (6); in the case where the reference distance $D_0$ is sufficiently larger than $Xe \cdot r_0/\tan\theta$ derived from the distance difference Xe, the denominator of the second term of Formula (9) can be regarded as 1. Consequently, the distance D can be calculated using Formula (10) below obtained by simplifying Formula (9). That is, the distance D can be expressed by the sum of the reference distance $D_0$ and a distance difference $r_0 d$. In the present embodiment, Formula (9) or Formula (10) is defined as a distance function.

[Math. 6]

$$D = D_0 + X_e r_0 / \tan\theta \quad (10)$$

The distance computation unit 130 calculates the distance D from the image capturing apparatus 20 to the measurement surface 5a on the basis of Formula (10), which is a distance function, for example. Then, the distance computation unit 130 outputs the calculated distance D to the focus adjustment unit 140.

After that, the focus adjustment unit 140 adjusts the position of the focus lens 22 of the image capturing apparatus 20 on the basis of the distance D from the image capturing apparatus 20 to the measurement surface 5a calculated in step S120 (S130). In the example illustrated in FIG. 5, when the measurement surface 5a of the measurement object 5 is deviated from the reference plane B, the linear light position X that appears in the captured image A is deviated from the reference linear light position $X_0$ by Xe in the X direction. As described above, in the case where the measurement surface 5a of the measurement object 5 is deviated from the reference plane B in a direction going away from the image capturing apparatus 20, the linear light position X is deviated to the right side of the drawing (i.e., the side opposite to the linear light irradiation apparatus 10) with respect to the linear light position $X_0$ as illustrated on the lower side of FIG. 5. In the case where the measurement surface 5a of the measurement object 5 is deviated from the reference plane B in a direction approaching the image capturing apparatus 20, the linear light position X is deviated to the left side of the drawing (the linear light irradiation apparatus 10 side) with respect to the reference linear light position $X_0$. When the linear light position X is thus deviated from the reference linear light position $X_0$, the focus lens 22 of the image capturing apparatus 20 is not focused on the measurement surface 5a. A captured image A acquired in a state where focus of the focus lens 22 of the image capturing apparatus 20 is not achieved is unclear, and when shape measurement processing described later is executed on the basis of the unclear captured image A, linear light appears thick in a shot image, which leads to a decrease in shape measurement precision of the measurement object 5.

Hence, the shape measurement apparatus 100 according to the present embodiment adjusts the focus position of the focus lens 22 of the image capturing apparatus 20 on the basis of the distance D between the image capturing apparatus 20 and the measurement object 5 by the focus adjustment unit 140. For example, in the case where the focus lens 22 according to the present embodiment is a motor drive lens including the motor 26 that rotates the focus ring 24, the focus adjustment unit 140 outputs a command to move the focus lens 22 to a predetermined distance position to the motor 26, on the basis of the distance D between the image capturing apparatus 20 and the measurement object 5. The predetermined distance position is a position such that focus is set on the measurement surface 5a of the measurement object 5 when the captured image A is acquired. This enables the image capturing apparatus 20 to acquire a clear captured image A. The focus adjustment unit 140 adjusts focus by causing the motor 26 to rotate the focus ring 24, on the basis of a correspondence relationship between the distance from the image capturing apparatus 20 to the measurement surface 5a and a rotation angle of the focus ring 24 at which focus is achieved, which is acquired in advance.

In this manner, the shape measurement apparatus 100 repeatedly performs processing of steps S110 to S130 each time a captured image A is acquired from the image capturing apparatus 20, thereby keeping a state where focus is set on the measurement surface 5a to enable a clear image to be acquired.

[2-2. Shape Measurement Processing]

The shape measurement apparatus 100 executes shape measurement processing (S140, S150) as well as the focus adjustment processing (S110 to S130).

Figure 6:
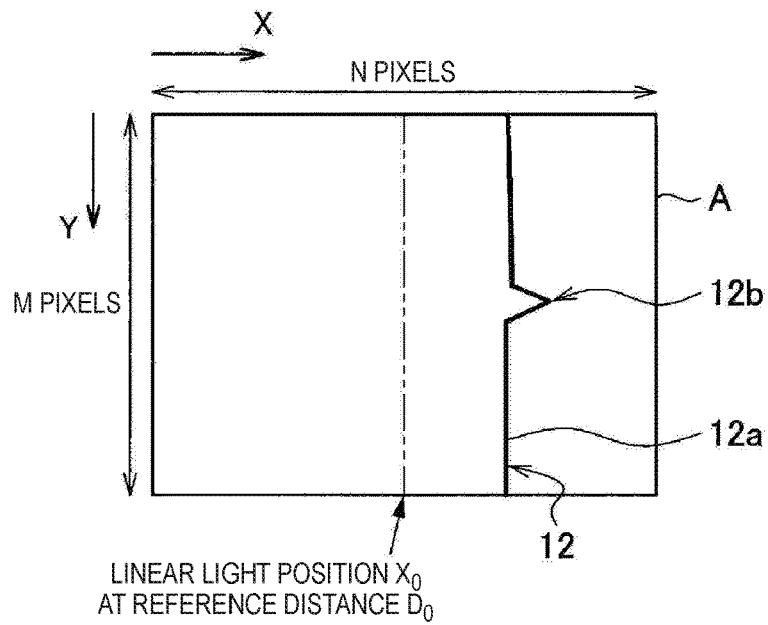
FIG. 6 is an explanatory diagram illustrating an example of a captured image of a measurement object having a convex shape on a measurement surface.

First, the shape computation unit 150 calculates the unevenness shape of the measurement surface 5a of the measurement object 5, on the basis of the degree of bend of the linear light in the captured image (S140). Here, FIG. 6 illustrates an example of the captured image A of the measurement object 5 having a convex shape on the measurement surface 5a. In the case where the measurement surface 5a is a flat surface without unevenness, straight linear light appears in the captured image A, whereas when there is a convex shape on the measurement surface 5a, linear light 12 including a straight part 12a and a bent part 12b caused by the convex shape on the measurement surface 5a appears in the captured image A, as illustrated in FIG. 6.

Here, the captured image A composed of N×M pixels captured at a time t is an image I(x,y|t) (0≤x≤N−1, 0≤y≤M−1). The shape computation unit 150 specifies a position in the horizontal direction (X direction) that exhibits the maximum luminance at each position in the vertical direction (Y direction) of the captured image A. That is, the shape computation unit 150 calculates an X coordinate $X_{max}(y|t)$ that gives the maximum luminance at each position in the vertical direction (Y direction) of the captured image A, on the basis of Formula (11) below.

[Math. 7]

$$X_{max}(y|t) = \underset{x}{\mathrm{argmax}}\, I(x, y|t) \quad (11)$$

A value (hereinafter also referred to as a "shape value") Z indicating the unevenness shape of the measurement object 5 measured at this time is acquired as a discrete value as in Formula (12) below, where the reference distance $D_0$ serves as the origin point of the shape.

[Math. 8]

$$Z(y|t) = \frac{X_{max}(y|t) - X_0}{\tan\theta} r \quad (12)$$

Note that an angle θ between the optical axis of the image capturing apparatus 20 and an emission direction of the linear light 12 of the linear light irradiation apparatus 10 is set to a value of 30° to 45°, and is normally set to 45°. The shape computation unit 150 finds the shape value Z for each of images continuously captured in a temporal direction, on the basis of Formula (12), thereby calculating the shape on the entire measurement surface 5a of the measurement object 5.

In addition, the shape computation unit 150 can calculate the discrete shape of the measurement surface 5a of the measurement object 5 on the basis of the shape value Z expressed by Formula (13) below, where an image capturing interval is Δt [sec] and the movement speed of the measurement object 5 is v [mm/sec]. Note that u is a discrete value (u=0, 1, 2, . . . ). The movement direction of the measurement object 5 is set as a u direction (the same direction as the X direction), and a direction orthogonal to this is set as a v direction (the same direction as the Y direction).

[Math. 9]

$$Z(u, v) = \frac{X_{max}(v|u\Delta t) - X_0}{\tan\theta} r \quad (13)$$

Furthermore, in the present embodiment, the shape computation unit 150 acquires the discrete shape in units of pixels of a captured image of the measurement surface 5a of the measurement object 5, on the basis of the X coordinate that gives the maximum luminance at each position in the vertical direction (Y direction) of the captured image A, which is obtained using Formula (11); however, the present invention is not limited to this example. For example, instead of the X coordinate $X_{max}(y|t)$ that gives the maximum luminance at each position in the vertical direction (Y direction) of the captured image A, a center-of-gravity position $X_g(y|t)$ expressed by Formula (14) below may be used. Using the center-of-gravity position $X_g(y|t)$ makes it possible to obtain a continuous value of the shape in the Y direction (v direction), which is not limited by a pixel resolution of a captured image.

[Math. 10]

$$X_g(y|t) = \frac{\sum_{x=0}^{N-1} I(x, y)x}{\sum_{x=0}^{N-1} I(x, y)} \quad (14)$$

In this manner, the shape computation unit 150 calculates the shape value Z, which is a variable indicating the shape of the measurement surface 5a of the measurement object 5. The shape computation unit 150 outputs the calculated shape value Z to the result output unit 160.

When the shape value Z indicating the shape of the measurement object 5 is received from the shape computation unit 150, the result output unit 160 outputs this calculation result to the display apparatus 30 or the storage unit 40 (S150). The display apparatus 30 displays the shape of the measurement object 5 on the basis of the shape value Z to notify an operator of the shape of the measurement object 5. In addition, the shape of the measurement object 5 stored in the storage unit 40 can be used as, for example, information for specifying a position having an unevenness shape on the measurement surface 5a of the measurement object 5.

The shape measurement apparatus 100 repeatedly performs processing of steps S140 and S150 each time a captured image A is acquired from the image capturing apparatus 20, to specify the shape of the measurement surface 5a of the measurement object 5. The captured image A used in the shape measurement processing is an image acquired by the focus adjustment processing described above. By calculating the shape of the measurement object 5 using a clear captured image, the shape measurement apparatus 100 can specify the shape of the measurement object 5 with higher precision.

As described above, when the image acquisition unit 110 acquires the captured image captured by the image capturing apparatus 20 (S100), the shape measurement apparatus 100 may execute focus adjustment processing (S110 to S130) and shape measurement processing (S140, S150) in parallel or alternately. For example, in the case of executing them alternately, focus is adjusted by focus adjustment processing (S110 to S130), and next, shape measurement processing (S140, S150) is executed on the same captured image as the shot image used for the focus adjustment processing.

Description has been given on focus adjustment processing of the image capturing apparatus 20 and shape measurement processing performed by the shape measurement apparatus 100 according to the present embodiment. According to the present embodiment, the distance between the image capturing apparatus 20 and the measurement object 5 is calculated from the linear light position of the linear light 12 that appears in the captured image A, without additional installation of a distance sensor, and the focus lens 22 is moved so that focus is set on a measurement surface at a position of the calculated distance. Thus, focus can be adjusted on the basis of a captured image acquired by the image capturing apparatus 20, without performing repeated processing such as sweeping of moving the position of the focus lens 22 in the optical axis direction, and a clear captured image can be obtained by the image capturing apparatus 20 without time delay. As a result, even when the distance between the image capturing apparatus 20 and the measurement object 5 changes, the position of the focus lens 22 can be adjusted in accordance with the change, which makes it possible to prevent linear light in a captured image from being blurred to be unclear, and maintain high precision of shape measurement.

The preferred embodiment(s) of the present invention has/have been described above with reference to the accompanying drawings, whilst the present invention is not limited to the above examples. A person skilled in the art may find various alterations and modifications within the scope of the appended claims, and it should be understood that they will naturally come under the technical scope of the present invention.

REFERENCE SIGNS LIST 5 measurement object
5a measurement surface
10 linear light irradiation apparatus
12 linear light
12a straight part
12b bent part
20 image capturing apparatus
22 focus lens
24 focus ring
26 motor
30 display apparatus
40 storage unit
100 shape measurement apparatus
110 image acquisition unit
120 linear light position detection unit
130 distance computation unit
140 focus adjustment unit
150 shape computation unit
160 result output unit
A captured image
B reference plane

The invention claimed is:

1. A shape measurement apparatus comprising:
a linear light position detection unit that detects, from a captured image of linear light applied to a measurement object by a linear light irradiation apparatus that is captured by an image capturing apparatus, a linear light position of the linear light;
a distance computation unit that computes a distance from the image capturing apparatus to the measurement object, on the basis of a distance difference between a reference linear light position detected by the linear light position detection unit when the measurement object is positioned at a position of a predetermined reference distance from the image capturing apparatus and the linear light position detected by the linear light position detection unit, the reference distance, and an angle formed by an optical axis of the image capturing apparatus and an emission direction of the linear light;
a focus adjustment unit that adjusts focus of the image capturing apparatus on the basis of the distance from the image capturing apparatus to the measurement object; and
a shape computation unit that computes a shape of the measurement object on the basis of the captured image, wherein the distance computation unit computes the distance from the image capturing apparatus to the measurement object on the basis of a distance function expressed using an image capturing resolution of the image capturing apparatus, and
wherein the distance computation unit computes a distance D from the image capturing apparatus to the measurement object on the basis of Formula (A) below, $$D = D_0 + \frac{X_e r_0 / \tan\theta}{1 - X_e r_0 / \tan\theta / D_0}, \quad (A)$$

where $D_0$ is the reference distance, $r_0$ is an image capturing resolution at the reference distance, Xe is a distance difference between the linear light position and the reference linear light position in units of pixels of the captured image, and $\theta$ is an angle formed by the optical axis of the image capturing apparatus and the emission direction of the linear light.

2. The shape measurement apparatus according to claim 1,
wherein the distance computation unit computes a distance D from the image capturing apparatus to the measurement object on the basis of Formula (B), instead of Formula (A), below, $$D = D_0 + X_e r_0 / \tan\theta \quad (B),$$

where $D_0$ is the reference distance, $r_0$ is an image capturing resolution at the reference distance, Xe is a distance difference between the linear light position and the reference linear light position in units of pixels of the captured image, and $\theta$ is an angle formed by the optical axis of the image capturing apparatus and the emission direction of the linear light.

3. The shape measurement apparatus according to claim 1,
wherein the linear light position detection unit
calculates a projection waveform expressing a sum of luminance values of pixels aligned in a straight-line direction of linear light at each position in a direction orthogonal to the straight-line direction of the linear light in the captured image, and
sets a peak position of the projection waveform as the linear light position.

4. The shape measurement apparatus according to claim 1,
wherein the linear light position detection unit
calculates a projection waveform expressing a sum of luminance values of pixels aligned in a straight-line direction of linear light at each position in a direction orthogonal to the straight-line direction of the linear light in the captured image, and
sets a center-of-gravity position of the projection waveform as the linear light position.

5. The shape measurement apparatus according to claim 1,
wherein the shape computation unit computes the shape of the measurement object on the basis of a maximum luminance position in a direction orthogonal to a straight-line direction of the linear light that is calculated for each position in the straight-line direction in the captured image.

6. The shape measurement apparatus according to claim 1,
wherein the shape computation unit computes the shape of the measurement object on the basis of a center-of-gravity position of luminance in a direction orthogonal to a straight-line direction of the linear light that is calculated for each position in the straight-line direction in the captured image.

7. A shape measurement method comprising:

a linear light position detection step of detecting, from a captured image of linear light applied to a measurement object by a linear light irradiation apparatus that is captured by an image capturing apparatus, a linear light position of the linear light;

a distance computation step of computing a distance from the image capturing apparatus to the measurement object, on the basis of a distance difference between a reference linear light position detected when the measurement object is positioned at a position of a predetermined reference distance from the image capturing apparatus and the linear light position, the reference distance, and an angle formed by an optical axis of the image capturing apparatus and an emission direction of the linear light;

a focus adjustment step of adjusting focus of the image capturing apparatus on the basis of the distance from the image capturing apparatus to the measurement object; and a shape computation step of computing a shape of the measurement object on the basis of the captured image, wherein the distance computation step of computing the distance from the image capturing apparatus to the measurement object on the basis of a distance function expressed using an image capturing resolution of the image capturing apparatus, and wherein the distance computation step of computing a distance D from the image capturing apparatus to the measurement object on the basis of Formula (A) below, $$D = D_0 + \frac{X_e r_0 / \tan\theta}{1 - X_e r_0 / \tan\theta / D_0}, \quad (A)$$

where $D_0$ is the reference distance, $r_0$ is an image capturing resolution at the reference distance, Xe is a distance difference between the linear light position and the reference linear light position in units of pixels of the captured image, and $\theta$ is an angle formed by the optical axis of the image capturing apparatus and the emission direction of the linear light.

8. The shape measurement method according to claim 7, wherein the distance computation step of computing a distance D from the image capturing apparatus to the measurement object on the basis of Formula (B) instead of Formula (A) below, $$D = D_0 + X_e r_0 / \tan\theta \quad (B),$$

where $D_0$ is the reference distance, $r_0$ is an image capturing resolution at the reference distance, Xe is a distance difference between the linear light position and the reference linear light position in units of pixels of the captured image, and $\theta$ is an angle formed by the optical axis of the image capturing apparatus and the emission direction of the linear light.

* * * * *